United States Patent
Galli et al.

(10) Patent No.: US 6,908,927 B2
(45) Date of Patent: Jun. 21, 2005

(54) PYRIDOPYRANOAZEPINE DERIVATIVES, THEIR PREPARATION AND THEIR THERAPEUTIC APPLICATION

(75) Inventors: Frédéric Galli, Vaucresson (FR); Samir Jegham, Montferrier-sur-Lez (FR); Alistair Lochead, Charenton (FR); Axelle Samson, Charenton (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/359,881

(22) Filed: Feb. 6, 2003

(65) Prior Publication Data

US 2003/0187012 A1 Oct. 2, 2003

Related U.S. Application Data

(63) Continuation of application No. 09/913,679, filed as application No. PCT/FR00/00502 on Mar. 1, 2000, now Pat. No. 6,538,003.

(30) Foreign Application Priority Data

Mar. 5, 1999 (FR) .............................. 99 02784

(51) Int. Cl.⁷ ..................... A61K 31/439; A61K 31/44; A61K 31/436; C07D 491/22; A61P 25/04
(52) U.S. Cl. ................... 514/286; 514/214.03; 546/63; 546/72; 544/581
(58) Field of Search ................. 540/581; 514/214.03, 514/286; 546/63

(56) References Cited

U.S. PATENT DOCUMENTS 6,143,761 A 11/2000 Lochead et al.

FOREIGN PATENT DOCUMENTS

| FR | 2761072 | 9/1998 |
| WO | WO 97/11072 | 3/1997 |

OTHER PUBLICATIONS

Nordvall et al., J. Medicinal Chemistry, vol. 39, No. 17, pp. 3269–3277, (1996).
Derwent Patent Abstract No. 199844 (2001).
Gopalakrishnan et al., European Journal of Pharmacology, 290 (1995), 237–246.
Levin, ED, Simon BB, Psychopharmacology (Berl) Aug. 1998:138(3–4):217–30.

*Primary Examiner*—Evelyn Mei Huang
(74) *Attorney, Agent, or Firm*—Michael D. Alexander

(57) ABSTRACT

The invention relates to pyridopyranoazepine derivatives, to pharmaceutical compositions containing them, to process for preparing them, and to the method of use thereof in the treatment or prevention of disorders associated with a dysfunction of the nicotine receptors.

6 Claims, No Drawings

PYRIDOPYRANOAZEPINE DERIVATIVES, THEIR PREPARATION AND THEIR THERAPEUTIC APPLICATION

CROSS REFERENCE TO THE RELATED APPLICATIONS

This application is a continuation of prior application Ser. No. 09/913,679 filed Aug. 17, 2001, now U.S. Pat. No. 6,538,003 which in turn is a 35 U.S.C. §371 application of PCT International application No. PCT/FR00/00502, filed Mar. 1, 2000, which in turn claims priority from French application No. 99/02784 filed 05 Mar. 1999.

The present invention relates to compounds of general formula (I)

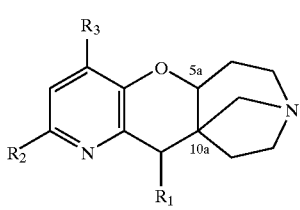

in which
$R_1$, is a hydrogen atom, a $(C_1-C_4)$alkyl group, a phenyl $(C_1-C_4)$alkyl group, a phenylhydroxy$(C_1-C_4)$alkyl group, a furanyl$(C_1-C_4)$alkyl group, or a furanyl-hydroxy $(C_1-C_4)$alkyl group, $R_2$ is either a hydrogen or halogen atom or a trifluoromethyl, cyano, hydroxyl, nitro, acetyl, $(C_1-C_6)$alkyl or $(C_1-C_6)$ alkoxy group or a group of general formula $NR_4R_5$ in which $R_4$ is a hydrogen atom or a $(C_1-C_4)$alkyl or $(C_1-C_4)$alkanoyl group and $R_5$ is a hydrogen atom or a $(C_1-C_4)$alkyl group, or else $R_4$ and $R_5$ form, with the nitrogen atom which carries them, a $C_4-C_7$ ring, or a phenyl or naphthyl group optionally substituted by a halogen atom or a trifluoromethyl, trifluoromethoxy, cyano, hydroxyl, nitro, acetyl, $(C_1-C_6)$alkyl, $(C_1-C_6)$ alkoxy or methylenedioxy group linked in the 2 and 3 positions of the phenyl ring, and $R_3$ is a hydrogen or halogen atom or a $(C_1-C_4)$alkyl group.

The compounds of general formula (I) can exist in the state of bases or of addition salts to acids. In addition, the atoms in positions 5a and 10a being asymmetric, a compound can exist in the form of pure geometric and optical isomers or of mixtures of the latter.

According to the invention, it is possible to prepare the compounds of general formula (I) by a process illustrated by the scheme which follows.

Scheme

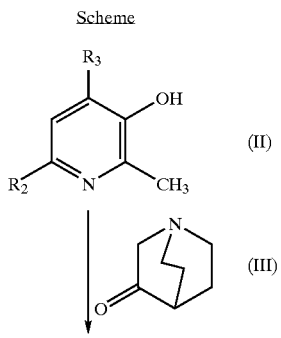

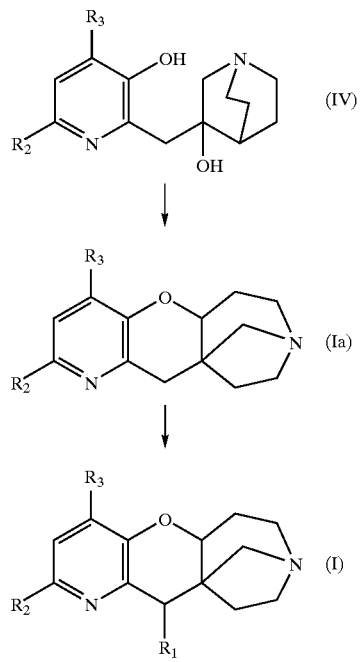

A 2-methylpyridin-3-ol of general formula (II), in which $R_2$ and $R_3$ are as defined above, is reacted with an alkyllithium, then the intermediate thus obtained is condensed with 1-azabicyclo[2.2.2]octan-3-one of formula (III), at low temperature and in an aprotic solvent such as tetrahydrofuran.

A compound of general formula (IV) is obtained, in which it is possible, if desired, to introduce or modify the substituents $R_2$ and $R_3$ according to any method known by the person skilled in the art.

The compound of general formula (IV) is then subjected to a dehydration, which is accompanied by a rearrangement, in acid medium, for example methanesulphonic acid or sulphuric acid at high temperature.

A compound of general formula (Ia) is obtained, in which it is possible to modify the $R_2$ and $R_3$ substituents and/or to introduce the $R_1$ substituent according to any method known to the person skilled in the art.

The starting compounds of formulae (II) and (III) are commercially available ($R_2=R_3=H$) or can be prepared according to known methods.

The examples which follow illustrate the preparation of some compounds of the invention. The elemental microanalyses, and the I.R. and N.M.R. spectra, as well as the X-ray diffraction spectra, in certain cases, confirm the structures of the compounds obtained.

The numbers indicated in brackets in the titles of the examples correspond to those of the 1st column of the table given further on.

In the names of the compounds, the dash "—" is part of the word, and the dash "_" only serves for the splitting at the end of the line; it is to be suppressed in the absence of splitting, and must not be replaced either by a normal dash or by a space.

EXAMPLE 1 (COMPOUND NO. 1)

(trans)-5a,6,7,9,10,11-hexahydro-8,10a-methanopyrido [2',3':5,6]pyrano[2,3-d]azepine hydrochloride (2:1)

1.1. 3-[(3-Hydroxypyridin-2-yl)methyl]-1-azabicyclo [2.2.2]octan-3-ol.

52.9 g (484 mmol) of 2-methyl-3-hydroxypyridine dissolved in 1300 ml of tetrahydrofuran are introduced into a 2000 ml three-neck flask under argon. The solution is cooled to −56° C. and 750 ml (975 mmol) of a 1.3 M 1-methylpropyllithium solution in cyclohexane is added dropwise in the course of 3 h, keeping the temperature lower than −50° C. At the end of the addition, the temperature is allowed to rise to −4° C. in the course of 45 min and the mixture is then again cooled to −58° C. to add 60.6 g (484 mmol) of 1-azabicyclo[2.2.2]octan-3-one dissolved in 250 ml of tetrahydrofuran dropwise in the course of 40 min. The temperature is allowed to rise to ambient and stirring is maintained for 20 h. The reaction mixture is cooled to 4° C. and hydrolysed by addition of 110 ml of an aqueous solution of 36% hydrochloric acid. 400 ml of water are added, the two phases are allowed to settle and the organic phase is extracted with water. The aqueous phases are reunited, the mixture is cooled to 4° C. and a concentrated aqueous solution of sodium hydroxide is added to pH 8.4. The precipitate obtained is filtered and dried in vacuo at 80° C.

62.5 g of product are thus obtained.

Melting point: 270–272° C.

1.2. (trans)-5a,6,7,9,10,11-hexahydro-8,10a-methanopyrido[2',3':5,6]pyrano[2,3-d]azepine hydrochloride (2:1).

2.34 g (10 mmol) of 3-[(3-hydroxypyridin-2-yl)methyl]-1-azabicyclo[2.2.2]octan-3-ol dissolved in 10 ml of methanesulphonic acid are introduced into a 50 ml flask and heated at 180° C. for 48 h.

The reaction mixture is cooled and poured onto ice. It is rendered alkaline by addition of a concentrated aqueous solution of sodium hydroxide and extracted with chloroform. The organic phase is dried over magnesium sulphate and concentrated under reduced pressure. The residue is purified by chromatography on a silica gel column by eluting with a 90/10/1 mixture of chloroform, methanol and ammonia. The product is obtained in base form, which is salified by addition of a solution of hydrochloric acid in ethanol. 1.55 g of hydrochloride are isolated.

Melting point: >300° C.

EXAMPLE 2 (COMPOUND NO. 2)

(5AS,10aR)-5a,6,7,9,10,11-hexahydro-8,10a-methano pyrido[2',3'1:5,6]pyrano[2,3-d]azepine hydrochloride (2:1)

2.1. (5aS,10aR)-5a,6,7,9,10,11-hexahydro-8,10a-methanopyrido [2',3':5,6]pyrano[2,3d]azepine (3R,5R)-(−)-O,O'-dibenzoyl-L-tartrate (1.2).

15.335 g (0.0709 mol) of (trans)-5a,6,7,9,10,11-hexahydro-8,10a-methanopyrido[2',3':5,6]pyrano[2,3-d]azepine in 50 ml of ethyl acetate are introduced into a 500 ml flask. A solution of 50.83 g (0.142 mol) of (3R,5R)-(−)-O,O'-dibenzoyl-L-tartaric acid in 50 ml of ethyl acetate is added, the solvent is evaporated under reduced pressure and the residue is dissolved in 885 ml of a 7/3 mixture of water and ethanol at reflux. After cooling, the crystals obtained are collected by filtration and recrystallized in 50 ml of hot propan-2-ol.

After cooling, 13.7 g of crystals are obtained.

Melting point: 145–148° C.; $[\alpha]_D^{20}$=−104.3° (c=0.5, MeOH).

2.2. (5aS,10aR)-5a,6,7,9,10,11-hexahydro-8,10a-methanopyrido [2',3':5,6]pyrano[2,3-d]azepine hydrochloride (2:1).

The treatment of the preceding compound with an aqueous solution of potassium carbonate followed by an extraction with dichloromethane allows 3.1 g (0.0143 mol) of compound in base form to be obtained.

Melting point: 69–71° C. $[\alpha]_D^{20}$=75.4° (c=1, MeOH).

This base is dissolved in 10 ml of ethanol in a 50 ml flask, 6 ml (0.030 mol) of a solution of 6 M hydrochloric acid in propan-2-ol is added, the mixture is concentrated to dryness under reduced pressure, the residue is taken up again in 40 ml of propan-2-ol, the mixture is heated to reflux and 5 ml of ethanol are added. After cooling, the crystals obtained are collected by filtration and dried under reduced pressure.

3.4 g of white crystals are obtained.

Melting point: 330° C.; $[\alpha]_D^{20}$=−85.3° (c=1, MeOH).

EXAMPLE 3 (COMPOUND NO. 4)

(trans)-2-Bromo-5a,6,7,9,10,11-hexahydro-8,10a-methano pyrido[2',3':5,6]pyrano[2,3-d]azepine 3.1. 3-[(6-Bromo-3-hydroxypyridin-2-yl)methyl]-1-azabicyclo[2.2.2]octan-3-ol.

52.23 g (0.223 mol) of 3-[(3-hydroxypyridin-2-yl)methyl]-1-azabicyclo[2.2.2.]octan-3-ol suspended in 500 ml of water at ambient temperature are introduced into a 1000 ml flask. 26.7 g (0.669 mol) of sodium hydroxide dissolved in 350 ml of water and 26.5 g (0.223 mol) of potassium bromide are added and the mixture is stirred until dissolution is complete before adding 11.5 ml (0.223 mol) of bromine dropwise in the course of 2 h.

The mixture is stirred for 18 h at ambient temperature, then the reaction mixture is neutralized by addition of 23 ml of acetic acid. It is cooled in an ice bath and the precipitate obtained is filtered. The mother liquors are concentrated and the precipitate obtained is triturated in propan-2-ol, filtered and rinsed.

27.9 g of product are obtained.

Melting point: 215–221° C.

3.2. (trans)-2-Bromo-5a,6,7,9,10,11-hexahydro-8,10a-methanopyrido [2',3':5,6]pyrano[2,3-d]azepine.

6.1 g of 3-[(6-bromo-3-hydroxypyridin-2-yl)methyl]-1-azabicyclo[2.2.2]octan-3-ol and 50 ml of concentrated sulphuric acid are introduced into a 100 ml flask. The mixture is heated at 130° C. for −72 h, then cooled to ambient temperature and poured onto ice. The aqueous phase is rendered alkaline to pH 10 by addition of a concentrated aqueous solution of sodium hydroxide and extracted with chloroform. The organic phases are dried over magnesium sulphate and concentrated under reduced pressure. The residue is purified by chromatography on a silica gel column by eluting with a 90/10/4 mixture of dichloromethane, methanol and ammonia.

1.2 g of product are obtained.

Melting point: 157–159° C.

EXAMPLE 4 (COMPOUND NO. 28)

(trans)-(−)-2-Bromo-5a,6,7,9,10,11-hexahydro-8, 10a-methanopyrido[2',3':5,6]pyrano[2,3-d]azepine hydrobromide (1:1)

4.1. (5aS,10aR)-2-Bromo-5a,6,7,9,10,11-hexahydro-8,10a-methanopyrido[2',3':5,6]pyrano[2,3-d]azepine (3R,5R)-(−)-O,O'-dibenzoyl-L-tartrate (1:2).

0.3 g (1 mmol) of (trans)-2-bromo-5a,6,7,9,10,11-hexahydro-8,10a-methanopyrido[2',3':5,6]pyrano[2,3-d] azepine dissolved in 10 ml of ethyl acetate is introduced into a 50 ml flask, 0.358 g (1 mmol) of O,O'-(−)-dibenzoyl-L-tartaric acid dissolved in 3 ml of ethyl acetate is added, the solvent is evaporated under reduced pressure and the residue is recrystallized in 5 ml of hot propan-2-ol. After cooling, the crystals obtained are collected by filtration and dried in vacuo.

0.12 g of crystals is obtained.

Melting point: 200° C. $[\alpha]_D^{10}=-106°$ (c=0.5, MeOH).

4.2. (trans)-(−)-2-Bromo-5a,6,7,9,10,11-hexahydro-8,10a-methanopyrido [2',3':5,6]pyrano[2,3-d]azepine hydrobromide (1:1).

The conversion to the base is carried out by treatment of the preceding compound with an-aqueous solution of sodium hydroxide, followed by an extraction with dichloromethane. 0.3 g (1 mmol) of base is dissolved in 30 ml of propan-2-ol in a 100 ml flask. 0.36 ml (2 mmol) of a solution of 33% hydrobromic acid in acetic acid is added. After cooling to 4° C., the crystals obtained are collected by filtration and dried in vacuo.

0.25 g of white crystals is obtained.

Melting point: 350–352° C.; $[\alpha]_D^{20}=-76.3°$ (c=0.5, MeOH).

EXAMPLE 5 (COMPOUND NO. 24)

(trans)-(−)-2-Chloro-5a,6,7,9,10,11-hexahydro-8,10a-methanopyrido[2',3':5,6]pyrano[2,3-d]azepine hydrochloride (2:1)

0.2 g (0.68 mmol) of (trans)-(−)-2-bromo-5a,6,7,9,10,11-hexahydro-8,10a-methanopyrido_[2',3':5,6]pyrano[2,3-d] azepine is dissolved in 4 ml of a concentrated aqueous solution of hydrochloric acid and heated at 180° C. in a sealed tube for 48 h.

The aqueous phase is evaporated and the residue is recrystallized in propan-2-ol.

0.075 g of crystals is obtained.

Melting point: 339–344° C.; $[\alpha]_D^{20}=-81°$ (c=0.5, MeOH).

EXAMPLE 6 (COMPOUND NO. 27)

(trans)-2-Cyano-5a,6,7,9,10,11-hexahydro-8,10a-methanopyrido[2',3':5,6]pyrano[2,3-d]azepine hydrobromide (1:1)

0.45 g (1.52 mmol) of (trans)-2-bromo-5a,6,7,9,10,11-hexahydro-8,10a-methanopyrido[2',3':5,6-]pyrano[2,3-d] azepine is dissolved in 8 ml of pyridine in a 50 ml flask, 0.205 g (2.29 mmol) of copper cyanide is added and the mixture is heated to reflux for 30 h. 75 ml of dichloromethane are added and the organic phase is washed with 45 ml of a saturated aqueous solution of ammonium chloride, then with 75 ml of water. After drying and concentration of the organic phase under reduced pressure, 0.22 g of expected product is obtained. It is dissolved in propan-2-ol and treated with one equivalent of hydrobromic acid dissolved at 33% in acetic acid. After cooling, collection of the crystals by filtration and drying in vacuo, 0.21 g of product is obtained.

Melting point: 329–332° C.

EXAMPLE 7 (COMPOUND NO. 10)

(trans)-2-(4-Methylphenyl)-5a,6,7,9,10,11-hexahydro-8,10a-methanopyrido[2',3':5,6]pyrano[2,3-d]azepine hydrobromide (2:1)

0.3 g (1 mmol) of (trans)-2-bromo-5a,6,7,9,10,11-hexahydro-8,10a-methanopyrido[2',3':5,6]pyrano[2,3-d] azepine in 6 ml of toluene, 0.193 g (1.4 mmol) of 4-methylphenylboronic acid, 0.072 g (0.06 mmol) of tetrakis (triphenyl)phosphine palladium, 1 ml (2 mmol) of sodium carbonate in 2 M aqueous solution and 0.05 ml of ethanol are introduced into a 10 ml reactor, and the reaction mixture is heated to reflux for 72 h. After settling, the organic phase is placed on silica gel and eluted with a 97/3/0.3 mixture of dichloromethane, methanol and ammonia.

0.31 g of product is obtained which is salified with two equivalents of hydrobromic acid dissolved in acetic acid.

Melting point: 355° C.

EXAMPLE 8 (COMPOUND NO. 5)

(trans)-11-Methyl-5a,6,7,9,10,11-hexahydro-8,10a-methanopyrido[2',3':5,6]pyrano[2,3-d]azepine hydrochloride (2:1)

(trans)-5a,6,7,9,10,11-hexahydro-8,10a-methano_pyrido [2',3':5,6]pyrano[2,3-d]azepine in 20 ml of anhydrous tetrahydrofuran is introduced into a 100 ml three-neck flask, the reaction mixture is cooled to −78° C. to add 1.2 ml (3 mmol) of 2.5 M butyllithium in hexane dropwise, and stirring is continued at −78° C. for 30 min.

0.19 ml (3 mmol) of iodomethane is added and the mixture is allowed to warm slowly to ambient temperature before adding 100 ml of water and extracting with dichloromethane. The organic phase is dried over magnesium sulphate, it is evaporated under reduced pressure and the residue is purified by chromatography on a silica gel column by eluting with a 90/10/1 mixture of dichloromethane, methanol and ammonia. The product obtained is treated with two equivalents of hydrochloric acid dissolved in propan-2-ol and 0.15 g of crystals is isolated by filtration.

Melting point: >330° C.

EXAMPLE 9 (COMPOUND NO. 9)

(trans)-α-Furan-3-yl-5a,6,7,9,10,11-hexahydro-10aH-8,10a-methanopyrido[2',3':5,6]pyrano[2,3-d] azepine-11-methanol hydrobromide (2:1)

0.43 g (2 mmol) of (trans)-5a,6,7,9,10,11-hexahydro-8,10a-methanopyrido[2',3':5,6]pyrano[2,3-d]azepine is treated with furan-3-carboxaldehyde under the conditions described in Example 8.

After salification with 2 equivalents of hydrobromic acid in acetic acid, 0.3 g of compound is obtained.

Melting point: 69–73° C. with decomposition.

EXAMPLE 10 (COMPOUND NO. 26)

(trans)-2-4-Dibromo-5a,6,7,9,10,11-hexahydro-8,10a-methanopyrido[2',3':5,6]pyrano[2,3-d]azepine hydrobromide (1:1)

10.1. 3-[(4,6-Dibromo-3-hydroxypyridin-2-yl)methyl]-1-azabicyclo[2.2.2]octan-3-ol.

A solution of 24 g (0.426 mol) of potassium hydroxide in 600 ml of water is introduced into a 2000 ml flask, 50.0 g (0.213 mol) of 3-[(3-hydroxypyridin-2-yl)_methyl]-1-azabicyclo[2.2.2.]octan-3-ol, and then, dropwise in the course of 40 min, a solution of 10.93 ml (0.213 mol) of bromine and 152.4 g (1.280 mol) of potassium bromide in 600 ml of water is added, and the mixture is stirred at ambient temperature for 16 h. The pH of the mixture is adjusted to 7.5 by addition of acetic acid, and it is stirred for 1 h. It is filtered, the solid obtained is dried, it is taken up in 1000 ml of ethanol, and the suspension obtained is heated for 2 h.

After cooling, the precipitate is collected by filtration and dried.

21.24 g of solid are obtained.

Melting point. 260–265° C.

10.2. (trans)-2-4-Dibromo-5a,6,7,9,10,11-hexahydro-8,10a-methanopyrido[2',3':5,6]pyrano[2,3-d]_azepine hydrobromide (1:1).

10 g (25 mmol) of 3-[(4,6-dibromo-3-hydroxypyridin-2-yl)methyl]-1-azabicyclo[2.2.2]octan-3-ol are introduced into a 500 ml flask, 150 ml of concentrated sulphuric acid and 3.6 g (25 mmol) of phosphorus pentoxide are added and the mixture is heated at 150° C. for 48 h. It is cooled, poured on to 300 g of ice, the pH is adjusted to 10 by addition of ammonia and the mixture is extracted with chloroform. The organic phase is dried over sodium sulphate and filtered, the solvent is evaporated under reduced pressure and the residue is purified by chromatography on a silica gel column by eluting with a 98/2/0.2 mixture of chloroform, methanol and ammonia.

After salification of the solid obtained with one equivalent of hydrobromic acid in acetic acid, 3.53 g of hydrobromide are obtained.

Melting point: 320° C. with decomposition.

The table which follows illustrates the chemical structures and the physical properties of some compounds of the invention. In the columns, "$R_1$" and "$R_2$", "$C_6H_5$", "$C_6H_4$" and "$C_6H_3$" denote, respectively, non-substituted, monosubstituted or disubstituted phenyl groups. The substituents and their positions are indicated. "$C_4H_3O$" denotes a furan-3-yl group. "2-$C_{10}H_7$" denotes a naphthalen-2-yl group. The column "5a,10a" indicates the configuration of the chiral centres 5a and 10a and "+/−" denotes a racemate.

In the column "salt", "—" denotes a compound in the base state, "HCl" denotes a hydrochloride, "HBr" denotes a hydrobromide, "dbL" denotes a dibenzoyl-L-tartrate and "dbD" denotes a dibenzoyl-D-tartrate. The acid:base molar ratios are indicated.

In the column "M.p. (° C.)", "(d)" indicates a melting point with decomposition.

TABLE

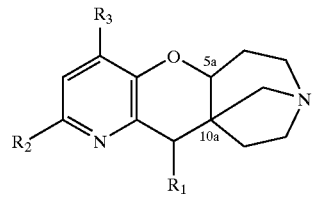

(I)

| No. | $R_1$ | $R_2$ | $R_3$ | 5a,10a | Salt | M.p. (° C.) | $[\alpha]^{20}_D$ (°) |
|---|---|---|---|---|---|---|---|
| 1 | H | H | H | (+/−) | HCl 2:1 | >300 | — |
| 2 | H | H | H | S,R | dbL 1:1 | 145–148 | −104.3 c = 0.5, MeOH |
|   |   |   |   |   | — | 69–71 | −75.4 c = 1, MeOH |
|   |   |   |   |   | HCl 2:1 | 330 | −85.3 c = 1, MeOH |
| 3 | H | H | H | R,S | — | 69–71 | +75 c = 1, MeOH |
| 4 | H | Br | H | (+/−) | — | 157–159 | — |
| 5 | $CH_3$ | H | H | (+/−) | HCl 2:1 | >330 | — |
| 6 | $CH_2CH_3$ | H | H | (+/−) | HBr 2:1 | 170 (d) | — |
| 7 | $CH_2C_6H_5$ | H | H | (+/−) | HBr 2:1 | 274–276 | — |
| 8 | $CH(OH)C_6H_5$ | H | H | (+/−) | HCl 2:1 | 231–233 | — |
| 9 | $CH(OH)$-3-$C_4H_3O$ | H | H | (+/−) | HBr 2:1 | 69–73 (d) | — |
| 10 | H | $C_6H_4$-4-$CH_3$ | H | (+/−) | HBr 2:1 | 355 | — |
| 11 | H | $C_6H_5$ | H | (+/−) | HBr 1:1 | 350–359 | — |
| 12 | H | $C_6H_4$-4-$OCF_3$ | H | (+/−) | — | 120–121 | — |
| 13 | H | $C_6H_4$-4-$CF_3$ | H | (+/−) | — | 120 | — |
| 14 | H | $C_6H_4$-3-$NO_2$ | H | (+/−) | — | 203 (d) | — |
| 15 | H | $C_6H_4$-3-$COCH_3$ | H | (+/−) | HBr2:1 | 260 | — |
| 16 | H | $C_6H_3$-3,4-$(OCH_2O)$ | H | (+/−) | HBr2:1 | 310 | — |
| 17 | H | $C_6H_3$-3,5-$(CF_3)_2$ | H | (+/−) | — | 102–103 | — |
| 18 | H | $C_6H_4$-4-F | H | (+/−) | HBr 2:1 | 302 | — |
| 19 | H | $C_6H_4$-4-$C_6H_5$ | H | (+/−) | HBr 2:1 | 350 | — |
| 20 | H | 2-$C_{10}H_7$ | H | (+/−) | — | 182 | — |
| 21 | H | Br | H | − | dbL 1:1 | 200 | −106 c = 0.7, MeOH |
| 22 | H | Br | H | + | dbD 1:1 | 214–217 | +108 c = 0.4, MeOH |
| 23 | H | Cl | H | (+/−) | HCl 2:1 | 280–281 | — |
| 24 | H | Cl | H | − | HCl 2:1 | 339–344 | −81 c = 0.5, MeOH |
| 25 | H | Cl | H | + | — | 82–85 | +94.1 c = 0.5, $CHCl_3$ |
| 26 | H | Br | Br | (+/−) | HBr 1:1 | 320 (d) | — |
| 27 | H | CN | H | (+/−) | HBr 1:1 | 329–332 | — |
| 28 | H | Br | H | − | HBr 1:1 | 350–352 | −76.3 c = 0.5, MeOH |

The compounds of the invention have been the subject of experiments which have demonstrated their therapeutic properties.

Thus they have been studied as to their affinity with respect to nicotinic receptors containing the $\alpha_4\beta_2$ subunit according to the methods described by Anderson and Arneric, *Eur. J. Pharmacol* (1994) 253 261, and by Hall et al., *Brain Res.* (1993) 600 127. 150 to 200 g male Sprague Dawley rats are decapitated and all of the brain is rapidly removed, homogenized in 15 volumes of a 0.32 M sucrose solution at 4° C. and then centrifuged at 1000 g for 10 min. The pellet is discarded, and the supernatant is centrifuged at 20,000 g for 20 min at 4° C. The pellet is recovered and homogenized with the aid of a Polytron™ mill in 15 volumes of double-distilled water at 4° C., and then centrifuged at 8000 g for 20 min. The pellet is discarded and the supernatant and the "buffy coat" are centrifuged at 40,000 g for 20 min, the pellet is recovered, resuspended in 15 ml of double-distilled water at 4° C. and centrifuged once more at 40,000 g before storing it at −80° C.

On the day of the experiment, the tissue is slowly thawed and suspended in 3 volumes of buffer. 150 µl of this membrane suspension are incubated at 4° C. for 120 min in the presence of 100 µl of 1 nM [$^3$H]cytisine in a final volume of 500 µl of buffer, in the presence or absence of compound to be tested. The reaction is stopped by filtration on Whatman GF/B™ filters previously treated with polyethyleneimine, the filters are rinsed with two times 5 ml of buffer at 4° C., and the radioactivity retained on the filter is measured by liquid scintigraphy. The non-specific binding is determined in the presence of 10 µM (−)-nicotine; the non-specific binding represents 75 to 85% of the total binding recovered on the filter. For each concentration of compound studied, the percentage of inhibition of the specific binding of [$^3$H]cytisine is determined, then the $IC_{50}$, the concentration of compound which inhibits 50% of the specific binding, is calculated. The $IC_{50}$ values of the most active compounds of the invention are between 0.08 and 1 µM.

The compounds of the invention have also been studied as regards their affinity with respect to nicotinic receptors containing the α7 subunit, according to the methods described by Marks and Collins, *J. Pharmacol. Exp. Ther.* (1982) 22 554 and Marks et al., *Mol. Pharmacol.* (1986) 30 427. 150 to 200 g male OFA rats are decapitated, all of the brain is rapidly removed, homogenized with the aid of a Polytron™ mill in 15 volumes of a 0.32 M sucrose solution at 4° C., then centrifuged at 1000 g for 10 min. The pellet is discarded, and the supernatant is centrifuged at 8000 g for 20 min at 4° C. The pellet is recovered and homogenized with the aid of a Polytron™ mill in 15 volumes of double-distilled water at 4° C., then centrifuged at 8000 g for 20 min. The pellet is discarded and the supernatant and the "buffy coat" are centrifuged at 40,000 g for 20 min. The pellet is recovered, resuspended with 15 volumes of double-distilled water at 4° C. and centrifuged once more at 40,000 g for 20 min before storing it at −80° C. On the day of the experiment, the tissue is slowly thawed and suspended in 5 volumes of buffer. 150 µl of this membrane suspension are preincubated at 37° C. for 30 min, in the dark, in the presence or absence of the compound to be tested. The membranes are then incubated for 60 min at 37° C., in the dark, in the presence of 50 µl of 1 nM [$^3$H]α-bungarotoxin in a final volume of 250 µl of 20 mM HEPES buffer with 0.05% of polyethyleneimine. The reaction is stopped by filtration on Whatman GF/C™ filters previously treated for 3 hours with 0.5% polyethyleneimine. The filters are rinsed with two times 5 ml of buffer at 4° C., and the radioactivity retained on each filter is measured by liquid scintigraphy. The non-specific binding is determined in the presence of α-bungarotoxin at 1 µM final concentration; the non-specific binding represents approximately 60% of the total binding recovered on the filter. For each concentration of compound studied, the percentage of inhibition of the specific binding of [$^3$H]α-bungarotoxin is determined, then the $IC_{50}$, the concentration of compound which inhibits 50% of the specific binding, is calculated. The $IC_{50}$ values of the compounds of the invention are between 1 and 20 µM.

The compounds of the invention have likewise been studied as regards their affinity with respect to peripheral nicotinic receptors of ganglionic type according to the method described by Houghtling et al., *Mol. Pharmacol,* (1995) 48 280–287.

The capacity of a compound to displace [$^3$H]-epibatidine from bovine adrenal gland membranes measures its affinity for this receptor.

Bovine adrenal glands stored at −80° C. are thawed and homogenized with the aid of a Polytron™ mill in 20 volumes of 50 mM Tris HCl buffer at pH 7.4 at 4° C., then they are centrifuged at 35,000 g for 10 min. The supernatant is discarded and the pellet is resuspended in 30 volumes of 50 mM Tris HCl buffer at 4° C. and rehomogenized before recentrifuging at 35,000 g for 10 min. The final pellet is taken up in 10 volumes of Tris HCl buffer at 4° C. 100 µl of membrane or 10 mg of fresh tissue are incubated at 24° C. for 3 h in the presence of 50 µl of 0.66 nM [$^3$H]-epibatidine in a final volume of 250 µl of buffer, in the presence or absence of compound to be tested. The reaction is stopped by dilution of the samples with 50 µM Tris HCl buffer pH 7.4 at 4° C. and then these are filtered on Whatman GF/C™ filters previously treated for 3 hours with 0.5% polyethyleneimine. The filters are rinsed two times with 5 ml of buffer and the radioactivity retained on the filter is measured by liquid scintigraphy. The non-specific binding is determined in the presence of (−)nicotine at 2 mM final concentration; the non-specific binding represents 30 to 40% of the total binding recovered on the filter. For each concentration of compound studied, the percentage of inhibition of the specific binding of [$^3$H]-epibatidine is determined, then the $IC_{50}$, the concentration of compound which inhibits 50% of the specific binding, is calculated.

The $IC_{50}$ values of the most active compounds of the invention are between 9 and 20 µM.

The results of the preceding tests show that certain compounds of the invention are selective ligands for the $\alpha_4\beta_2$ subunits of the nicotinic receptor.

The compounds of the invention were finally the subject of in vivo experiments which demonstrated their therapeutic properties. Thus, for example, they were studied in the hotplate model, according to the method of Eddy and Leimbach, *J. Pharmacol. Exp. Ther.* (1953) 107 385–393 with the aim of investigating and quantifying a possible analgesic effect. 20 to 30 g mice were subjected to a heat stimulus by contact of the paws with a plate maintained at a constant temperature of 57.5° C. by a thermostatted water bath. The time of reaction to the pain, which is manifested by licking of the paws or jumping, is measured. Thus, after the pretreatment period carried out by the subcutaneous or oral route (each batch being formed of eight animals for the same pretreatment), the mice are placed individually on the plate and the time of reaction to the pain is measured. The animal is removed from the plate immediately after manifestation of the pain. The maximum time of exposure to the stimulus is 30 s. The mean reaction time accompanied by the standard error of the mean (s.e.m.) is expressed for each batch. A non-parametric variance analysis (Kruskal-Wallis) is carried out on the entire batch. A Wilcoxon test allows the comparison of each treated batch with the control batch. The differences are considered as statistically significant at the 5% threshold.

This reaction time is significantly increased by the analgesics mainly with central effects.

The compounds of the invention show an activity in this test at doses of between 3 and 30 mg/kg by the intraperitoneal or oral route.

These results suggest the use of the compounds in the treatment or prevention of disorders associated with a dysfunction of the nicotinic receptors, especially at the level of the central nervous system or the gastrointestinal system.

At the level of the central nervous system, these disorders comprise cognitive impairments, more specifically memory impairments, but also attention impairments, associated with Alzheimer's disease, with pathological ageing (Age Associated Memory Impairment, AAMI), with Parkinson's disease, with mongolism (Down's syndrome), with Korsakoff's alcoholic syndrome, and with vascular dementia (multi-infarct dementia, MID).

The compounds of the invention could likewise be useful in the treatment of the motor disorders observed in Parkinson's disease or other neurological diseases such as Huntington's chorea, Tourette's syndrome, tardive dyskinesia and hyperkinesia.

The compounds of invention can likewise constitute a curative or symptomatic treatment of cerebral vascular accidents and cerebral hypoxic episodes. They can be used in the case of psychiatric pathologies: schizophrenia, depression, anxiety, panic attacks, compulsive and obsessive behaviour.

They can prevent the symptoms due to withdrawal from tobacco, alcohol and various substances inducing dependence, such as cocaine, LSD, cannabis and benzodiazepines.

Finally, they can be used for the treatment of pain.

At the level of the gastrointestinal system, the compounds of the invention could be used in the treatment of Crohn's disease, of ulcerative colitis, of irritable bowel syndrome and of obesity.

To this effect, the compounds of the invention can be present in any form of composition appropriate for enteral, parenteral or transdermal administration, such as tablets, sugar-coated tablets, hard and soft gelatin capsules, drinkable or injectable suspensions or solutions such as syrups or ampoules, transdermal patches, etc., combined with suitable excipients, and dosed to allow a daily administration of 0.01 to 20 mg/kg.

What is claimed:

1. A process for preparation of compound in the form of pure geometrical or optical isomers or a mixture of such isomers, of formula (I)

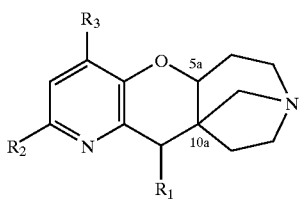

in which
$R_1$ is a hydrogen atom, a $(C_1-C_4)$alkyl group, a phenyl $(C_1-C_4)$alkyl group, a phenylhydroxy $(C_1-C_4)$ alkyl group, a furanyl$(C_1-C_4)$alkyl group, or a furanylhydroxy$(C_1-C_4)$alkyl group, $R_2$ is either a hydrogen or halogen atom or a trifluoromethyl, cyano, hydroxyl, nitro, acetyl, $(C_1-C_6)$ alkyl or $(C_1-C_6)$alkoxy group or a group of general formula $NR_4R_5$ in which $R_4$ is a hydrogen atom or a $(C_1-C_4)$alkyl or $(C_1-C_4)$alkanoyl group and $R_5$ is a hydrogen atom or a $(C_1-C_4)$alkyl group, or else $R_4$ and $R_5$ form, with the nitrogen atom which carries them, a $C_4-C_7$ ring, or a phenyl or naphthyl group optionally substituted by a halogen atom or a trifluoromethyl, trifluoromethoxy, cyano, hydroxyl, nitro, acetyl, $(C_1-C_6)$alkyl, $(C_1-C_6)$alkoxy or methylenedioxy group linked in the 2 and 3 positions of the phenyl ring, and $R_3$ is a hydrogen or halogen atom or a $(C_1-C_4)$alkyl group, in the state of a base or an addition salt to an acid wherein a compound of general formula (IV)

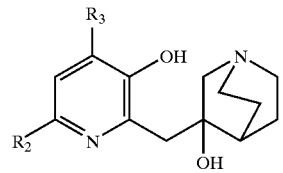

in which $R_2$ and $R_3$ are as defined above is subjected to a dehydration in acid medium followed by a rearrangement at high temperature, to obtain a compound of general formula (Ia)

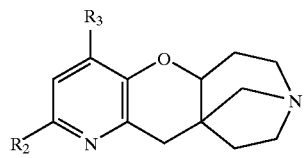

in which, if desired, the substituents $R_2$ and $R_3$ are modified into other $R_2$ or $R_3$ substituents and/or a substituent $R_1$ such as defined above is introduced to afford compounds of Formula I.

2. A method for the treatment or prevention of pain which comprises administering to a patient in need of such treatment an effective amount of a compound in the form of pure geometrical or optical isomers or a mixture of such isomers, of formula (I)

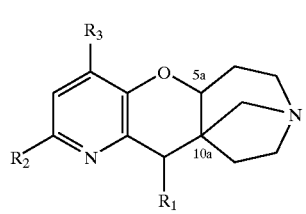

in which
$R_1$ is a hydrogen atom, a $(C_1-C_4)$alkyl group, a phenyl $(C_1-C_4)$alkyl group, a phenylhydroxy$(C_1-C_4)$alkyl group, a furanyl$(C_1-C_4)$alkyl group, or a furanylhydroxy$(C_1-C_4)$alkyl group, $R_2$ is either a hydrogen or halogen atom or a trifluoromethyl, cyano, hydroxyl, nitro, acetyl, $(C_1-C_6)$ alkyl or $(C_1-C_6)$alkoxy group or a group of general formula $NR_4R_5$ in which $R_4$ is a hydrogen atom or a $(C_1-C_4)$alkyl or $(C_1-C_4)$alkanoyl group and $R_5$ is a hydrogen atom or a $(C_1-C_4)$alkyl group, or else $R_4$ and $R_5$ form, with the nitrogen atom which carries them, a $C_4-C_7$ ring, or a phenyl or naphthyl group optionally substituted by a halogen atom or a trifluoromethyl, trifluoromethoxy, cyano, hydroxyl, nitro, acetyl, $(C_1-C_6)$alkyl, $(C_1-C_6)$alkoxy or methylenedioxy group linked in the 2 and 3 positions of the phenyl ring, and $R_3$ is a hydrogen or halogen atom or a $(C_1-C_4)$alkyl group, in the state of a base or an addition salt to an acid.

3. A method according to claim 2 wherein $R_1$ is hydrogen, methyl, ethyl, phenylmethyl, phenyl CH(OH)—, furanyl CH(OH); $R_2$ is hydrogen, bromo, phenyl, phenyl substituted by methyl, trifluoromethoxy, trifluoromethyl, nitro, acetyl, methylenedioxy, fluoro, naphthyl, chloro or cyano; and $R_3$ is hydrogen or bromo.

4. A method according to claim 3 wherein $R_1$ is hydrogen, methyl, ethyl, phenylmethyl, phenyl CH(OH), 3-furanyl CH(OH)-; $R_2$ is hydrogen, bromo, phenyl, 4-methylphenyl, 4-trifluoromethoxyphenyl, 4-trifluoromethylphenyl, 3-nitrophenyl, 3-acetylphenol, 3,4-methylene dioxyphenyl, 3,5-ditrifluoromethylphenyl, 4-fluorophenyl, 4-biphenyl, 2-naphthyl, chloro, or cyano; and R3 is hydrogen or bromo.

5. A method according to claim 4 wherein the compound is (5a S, 10aR)-5a,6,7,9,10,11-hexahydro-8,10a-methanopyrido [2',3':5,6]pyrano[2,3-d]azepine or an addition salt to an acid thereof.

6. A method according to claim 5 wherein the compound is (5a S, 10aR)-5a,6,7,9,10,11-hexahydro-8,10a-methanopyrido [2',3':5,6]pyrano[2,3-d]azepine hydrochloride (2:1).

* * * * *